（12) United States Patent
Small

(10) Patent No.: US 6,911,505 B2
(45) Date of Patent: Jun. 28, 2005

(54) SELECTIVE ISOMERIZATION AND LINEAR DIMERIZATION OF OLEFINS USING COBALT CATALYSTS

(75) Inventor: Brooke L. Small, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 22 days.

(21) Appl. No.: 10/264,730

(22) Filed: Oct. 4, 2002

(65) Prior Publication Data

US 2004/0068154 A1 Apr. 8, 2004

(51) Int. Cl.[7] ................................................. C08F 4/44
(52) U.S. Cl. .................... 526/130; 526/169.1; 526/171; 526/172; 526/161; 526/901; 526/348
(58) Field of Search ............................... 526/130, 169.1, 526/171, 172, 161, 901, 348

(56) References Cited

U.S. PATENT DOCUMENTS

| | | | |
|---|---|---|---|
| 4,320,243 A | 3/1982 | Chauvin et al. ............ | 585/521 |
| 5,955,555 A | 9/1999 | Bennett ...................... | 526/133 |
| 6,063,881 A | 5/2000 | Bennett ...................... | 526/161 |
| 6,103,946 A | 8/2000 | Brookhart, III et al. .... | 585/523 |
| 6,150,482 A | * 11/2000 | Brookhart et al. .......... | 526/161 |
| 6,291,733 B1 | 9/2001 | Small et al. ................. | 585/512 |
| 6,489,497 B1 | 12/2002 | Brookhart, III et al. .... | 556/138 |
| 2002/0177744 A1 | 11/2002 | Small et al. .................. | 585/16 |
| 2003/0149198 A1 * | 8/2003 | Small et al. ................. | 526/115 |

FOREIGN PATENT DOCUMENTS

| | | |
|---|---|---|
| GB | 1124123 | 8/1968 |
| GB | 1129463 | 10/1968 |

OTHER PUBLICATIONS

*Highly Active Iron and Cobalt Catalysts for the Polymerization of Ethylene,* Brooke L. Small, Maurice Brookhart, and Alison M.A. Bennett, *Journal of the American Chemical Society,* vol. 120, No. 16., pp. 4049–4050, 1998.
*Iron Catalysts for the Head–to–Head Dimerization of a–Olefins and Mechanistic Implications for the Production of Linear a–Olefins,* Brooke L. Small and A.J. Marcucci, *Organometallics,* vol. 20, No. 26, pp. 5738–5744, 2001.
International Search Report, PCT/US 03/29158, Feb. 23, 2004; 3 pages.

* cited by examiner

*Primary Examiner*—William K. Cheung
(74) *Attorney, Agent, or Firm*—Conley Rose, PC; Rodney B. Carroll; Joe D. Hulett

(57) ABSTRACT

Processes for the production of alpha-olefins, including dimerization and isomerization of olefins using a cobalt catalyst complex are provided herein. The olefins so produced are useful as monomers in further polymerization reactions and are useful as chemical intermediates.

93 Claims, 1 Drawing Sheet

Propylene dimers made by MMAO-activated cobalt complex 1d (53% 1-hexene)

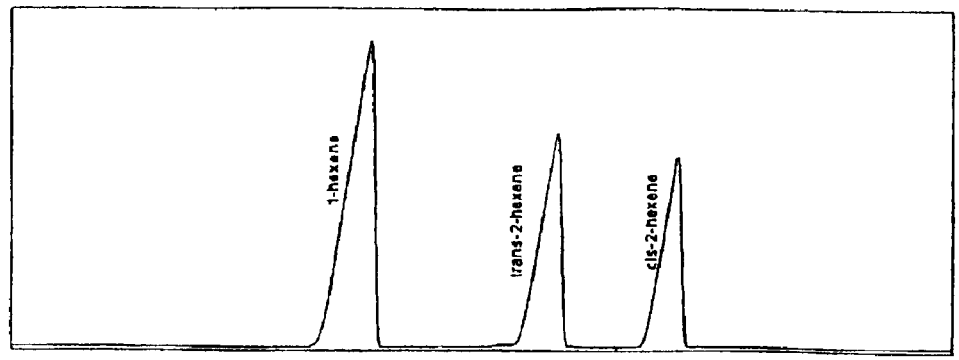
Figure 1 - Propylene dimers made by MMAO-activated cobalt complex Id (53% 1-hexene)
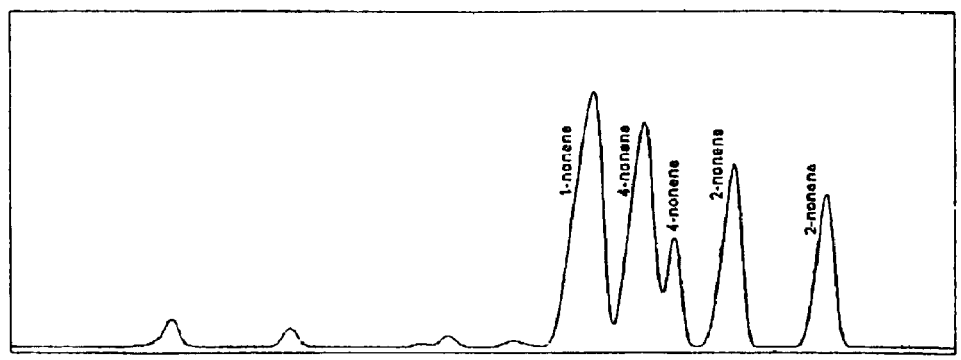
Figure 2 - Propylene trimers made by MMAO-activated cobalt complex Id (34% 1-nonene)

SELECTIVE ISOMERIZATION AND LINEAR DIMERIZATION OF OLEFINS USING COBALT CATALYSTS

FIELD OF THE INVENTION

This invention is in the field of olefin catalysis. Various olefins are produced by a process employing a tridentate cobalt catalyst.

BACKGROUND OF THE INVENTION

Alpha-olefins, especially those containing about 6 to about 20 carbon atoms, are important items of commerce, with about 1.5 million tons reportedly being produced in 1992. Alpha-olefins are also used as intermediates in the manufacture of detergents, as monomers (especially in linear low density polyethylene), and as intermediates for many other types of products. As a consequence, improved methods of making these compounds are of value.

The dimerization of olefins by transition metal complexes represents an important class of industrially relevant chemistry.[1] For example, ethylene dimerization to 1-butene can provide a source of comonomer in the production of polyethylene;[2] and olefins such as propylene and butene are dimerized to give $C_6$–$C_8$ materials that serve as feedstocks for gasoline blending or alcohol production.[3]

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as diethylaluminum chloride (DEAC). In all of these processes significant amounts of branched and/or internal olefins and/or diolefins, are produced. Since in most instances these are undesired, and often difficult to separate from the desired linear alpha-olefins, minimization of these byproducts is sought.

In the field of olefin catalysis, tridentate iron catalysts are known for the production of α-olefins. Examples of these iron catalysts may be found in U.S. Pat. No. 6,103,946, issued Aug. 15, 2000, the disclosure of which is herein incorporated by reference.

Additional cobalt based catalysts useful for the oligomerization of propylene are taught in U.S. Pat. No. 6,063,881, the disclosure of which is herein incorporated by reference.

Currently, there are no known methods to selectively make linear internal olefins or alpha-olefins from propylene.

The development of cobalt catalysts having enhanced selectivity and high productivity in the production of olefins and alpha-olefins is of value.

Thus, it would be a significant contribution to the art to provide cobalt catalysts for the production of olefins which have both good productivity and high selectivity.

SUMMARY OF THE INVENTION

The instant invention relates to processes for the production of alpha-olefins using tridentate cobalt catalysts.

The instant invention relates to processes for the dimerization of olefins using tridentate cobalt catalysts.

The invention further relates to processes for the isomerization of alpha-olefins to internal olefins using tridentate cobalt catalysts.

The invention still further relates to processes for the oligomerization of alpha-olefins by a step-growth process.

BRIEF DESCRIPTION OF THE DRAWINGS

FIG. 1 illustrates propylene dimers, specifically 1-hexene and 2-hexene (cis/trans), made employing a cobalt catalyst.

FIG. 2 illustrates propylene trimers, specifically 1-nonene, 2-nonene, and 4-nonene, made using a cobalt catalyst.

DETAILED DESCRIPTION OF THE INVENTION

The invention provides cobalt complexes useful in the production of alpha-olefins, and additionally the dimerization and isomerization of alpha-olefins. The cobalt complexes employed herein were shown to possess a higher degree of selectivity for producing linear dimers than their iron analogs[4], and are also highly selective for isomerizing the starting material.

The cobalt complex of formula I may be employed in the production of alpha-olefins:

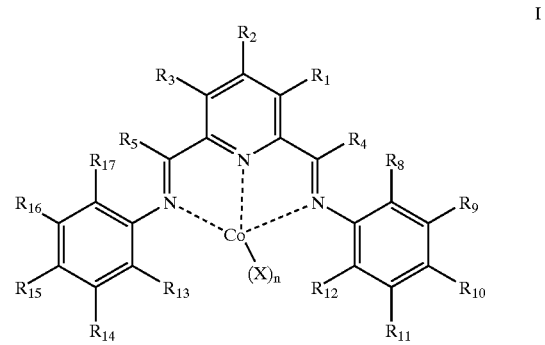

wherein:
each X is an anion;
n is 1, 2 or 3 so that the total number of negative charges on said anion or anions is equal to the oxidation state of a Co atom present in Formula I;
$R_1$, $R_2$ and $R_3$ are each independently hydrogen, hydrocarbyl, substituted hydrocarbyl, or an inert functional group;
$R_4$ and $R_5$ are each independently hydrogen, hydrocarbyl, an inert functional group or substituted hydrocarbyl;
$R_9$, $R_{10}$, $R_{11}$, $R_{14}$, $R_{15}$ and $R_{16}$ are each independently hydrogen, hydrocarbyl, an inert functional group or substituted hydrocarbyl;
$R_8$ and R17 are each hydrogen, fluorine, an inert functional group, a primary carbon group, a secondary carbon group or a tertiary carbon group;
and provided that:
when $R_8$ is a primary carbon group none, one or two of R12, R13 and R17 are primary carbon groups or inert functional groups, and the remainder of R12, R13, and R17 are hydrogen or fluorine;
when $R_8$ is a secondary carbon group, none or one or two of R12, R13 and R17 is a primary carbon group or a secondary carbon group or an inert functional group and the remainder of R12, R13, and R17 are hydrogen or fluorine;

when $R_8$ is a tertiary carbon group all of R12, R13, and R17 are hydrogen or fluorine; and any two of $R_8$, R9, R10, R11, R12, R13, R14, R15, R16 and R17 vicinal to one another, taken together may form a ring.

The following terms are provided.

A "hydrocarbyl group" is a univalent group containing only carbon and hydrogen. If not otherwise stated, it is preferred that hydrocarbyl groups herein contain 1 to about 30 carbon atoms. The terms "hydrocarbyl" and "alkyl" are equivalent, and may be used interchangeably.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR_{18}$ wherein $R_{18}$ is hydrocarbyl or substituted hydrocarbyl. In cases in which the functional group may be near a cobalt atom, such as R4, R5, $R_8$, R12, R13, and R17 the functional group should not coordinate to the cobalt atom more strongly than the groups in compounds containing R4, R5, $R_8$, R12, R13 and R17 which are shown as coordinating to the cobalt atom, that is they should not displace the desired coordinating group.

By an "alkyl aluminum compound" is meant a compound in which at least one alkyl group is bound to an aluminum atom. Other groups such as alkoxide, oxygen, and halogen may also be bound to aluminum atoms in the compound.

By "neutral Lewis base" is meant a compound, which is not an ion, which can act as a Lewis base. Examples of such compounds include ethers, amines, sulfides, and organic nitriles.

By "cationic Lewis acid" is meant a cation which can act as a Lewis acid. Examples of such cations are sodium and silver cations.

By "relatively noncoordinating (or weakly coordinating)" anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Strauss, Chem. Rev., vol. 93, p. 927–942 (1993), both of which are hereby included by reference. Among such anions are those formed from alkyl aluminum compounds, defined above, and X⁻, including $R^9_3AlX^-$, $R^9_2AlClX^-$, $R^9AlCl_2 X^-$, and "$R^9AlOX^-$". Other useful noncoordinating anions include BAF-{BAF=tetrakis [3,5-bis(trifluoromethyl)phenyl]borate}, $SbF_6^-$, $PF_6^-$, and $BF_4^-$, trifluoromethanesulfonate, p-toluenesulfonate, (Rf $SO_2)_2N^-$ (wherein Rf is perfluoroalkyl), and $(C_6F_5)_4B^-$.

By formation of an alpha-olefin is meant formation of a compound (or mixture of compounds) of the formula $H(CH_2CH_2)q$ $CH=CH_2$ wherein q is an integer of 1 to about 18. In most such reactions, a mixture of compounds will result which have differing values of q, and in most reactions to form the alpha-olefins some of the alpha-olefins formed will have q values of more than 18. Preferably less than 50 weight percent, more preferably less than 20 weight percent of the product mixture will have q values over 18. Because the product contains substantial amounts of internal olefins, the alpha-olefin process is selective for making linear products, but not specific for preparing the particular alpha-olefins. These must be separated by a suitable means, for example distillation, and the like.

By "an empty coordination site" is meant a potential coordination site that does not have a ligand bound to it. Thus if an olefin molecule is in the proximity of the empty coordination site, the olefin molecule may coordinate to the metal atom.

By a "primary carbon group" herein is meant a group of the formula —CH2—, wherein the free valence—is to any other atom (the bond represented by the hyphen is to the benzene ring to which the primary carbon group is attached). Thus the free valence—may be bonded to a hydrogen atom, halogen atom, a carbon atom, an oxygen atom, a sulfur atom, etc. In other words, the free valence—may be to hydrogen, hydrocarbyl, substituted hydrocarbyl or a functional group. Examples of primary carbon groups include—CH3, —CH2CH(CH3)2, —CH2Cl, —CH2C6H5, —OCH3 and —CH2OCH3.

By "a ligand that may add to an olefin" is meant a ligand coordinated to a metal atom into which an olefin molecule (or a coordinated olefin molecule) may insert to start or continue a process.

Compounds useful as ligands are diimines of 2,6-pyridinedicarboxaldehyde or 2,6-diacylpyridines, wherein all of the "R" groups are as defined above. Synthesis of these compounds is known in the art, and is further discussed in the Examples section herein.

In preferred compounds of Formula I, and all other preferred compounds in which the following "R" groups appear:

R4 and R5 are methyl or hydrogen; and/or
R1, R2, and R3 are all hydrogen; and/or
R9, R10, R11, R14, R15 and R16 are all hydrogen; and/or
R12 and R17 are each independently methyl, ethyl, propyl or isopropyl, more preferably both are methyl or ethyl; and/or each X is a monovalent anion, more preferably selected from the group consisting of halide and nitrile.

It is also preferred that in all compounds in which they appear:

if $R_8$ is a primary carbon group, R13 is a primary carbon group and R12 and R17 are hydrogen;
if $R_8$ is a secondary carbon group, R13 is a primary or secondary carbon group, more preferably a secondary carbon group, and R12 and R17 are hydrogen.

In all specific preferred compounds in which they appear it is preferred that:

R4 and R5 are methyl, R9, R10, R11, R14, R15 and R16 are all hydrogen, and R12 and R17 are both methyl;
R4 and R5 are methyl, R9, R10, R11, R14, R15 and R16 are all hydrogen, and R12 and R17 are both ethyl;
R4 and R5 are methyl, R9, R10, R14, R15 and R16 are all hydrogen, and R12 and R17 are both isopropyl;
R4 and R5 are methyl, R9, R10, R11, R14, R15 and R16 are all hydrogen, and R12 and R17 are both n-propyl;
R4 and R5 are methyl, R9, R10, R11, R14, R15 and R16 are all hydrogen, and R12 and 17 are both chloro; and
R4 and R5 are methyl, R9, R10, R11, R14, R15 and R16 are all hydrogen, and R12 and R17 are both trifluoromethyl.

In all of the above specific compounds it is preferred that X is selected from the group consisting of chloride, bromide and nitrate, and more preferably that it is chloride.

The cobalt complexes may be formed by reacting the appropriate tridentate ligand with a cobalt salt, such as a cobalt halide or a compound such as cobalt [II] nitrate. See Example 1 for the preparation of these cobalt complexes.

In the first process to produce alpha-olefins described herein a cobalt complex of Formula I is contacted with ethylene and a neutral Lewis acid W capable of abstracting X⁻, hydride or alkyl (R20) from a compound of Formula I to form a weakly coordinating anion, and must alkylate or be capable of adding a hydride ion to the cobalt atom, or an additional alkylating agent or an agent capable of adding a hydride anion to the cobalt atom must be present. The neutral Lewis acid is originally uncharged (for example, not ionic). Suitable neutral Lewis acids include SbF5, Ar3B (wherein Ar is aryl), BF3, alkylalumoxanes, and trialkylaluminum compounds. Suitable cationic Lewis acids or Bronsted acids include NaBAF, silver trifluoromethanesulfonate, HBF4, or [C6H5 NH(CH3)2]+[B(C6 F5)4]⁻. In those instances in which (a compound of Formula I (and similar catalysts which require the presence of a neutral Lewis acid or a cationic Lewis or Bronsted acid), does not contain an alkyl or hydride group already bonded to the cobalt atom, the neutral Lewis acid or a cationic Lewis or Bronsted acid also alkylates or adds a hydride to the cobalt or a separate alkylating or hydriding agent is present, for example, causes an alkyl group (R20) or hydride to become bonded to the cobalt atom.

It is preferred that $R_{20}$ contains 1 to 4 carbon atoms, and more preferred that $R_{20}$ is methyl or ethyl.

For instance, alkyl aluminum compounds may alkylate compounds of Formula I. However, not all alkylaluminum compounds may be strong enough Lewis acids to abstract X⁻ or an alkyl group from the cobalt atom. In that case a separate Lewis acid strong enough to do the abstraction must be present. For instance, (C6 F5)3B or (C6 H5)3 B are useful Lewis acids, and could be used in combination with, for example, an alkylaluminum compound such as triethylaluminum.

A preferred neutral Lewis acid, which can alkylate the cobalt, is a selected alkyl aluminum compound, such as R193 Al, R19 AlCl2, R192AlCl2, and "R19 AlO" (alkylaluminoxanes), wherein R19 is alkyl containing 1 to 25 carbon atoms, preferably 1 to 4 carbon atoms. Suitable alkyl aluminum compounds include methylaluminoxanes (which are oligomers with the general formula [MeAlO]n), (C2 H5)2 AlCl, C2 H5 AlCl2, and [(CH3)2 CHCH2]3 Al.

Metal hydrides such as $NaBH_4$ may be used to bond hydride groups to the Co.

In another process, a cobalt complex of Formula III is either added to the process or formed in situ in the process. Complexes may be added directly to the process or formed in situ. In fact, more than one such complex may be formed during the course of the process, for instance formation of an initial complex and then reaction of that complex to form an active ended oligomer containing such a complex.

Examples of such complexes which may be formed initially in situ include compounds of Formula III

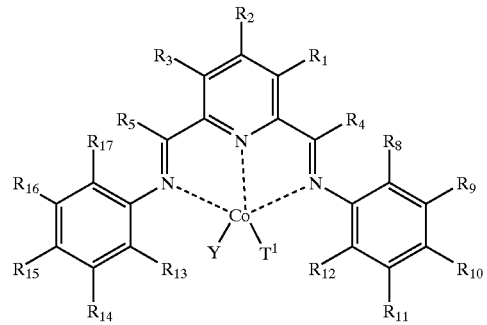

III and wherein the "R" substituents are as defined above, T1 is hydride or alkyl or any other anionic ligand into which ethylene can insert, Y is a vacant coordination site, or a neutral ligand capable of being displaced by ethylene.

For instance, a compound of Formula III may be formed by the reaction of a compound of Formula I with a neutral Lewis acid such as an alkyl aluminum compound.

Another method of forming such a complex in situ is combining a suitable cobalt compound such as cobalt chloride, a compound of Formula II

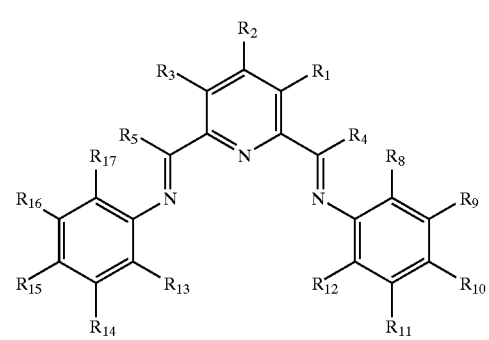

II where the R groups are as defined above and an alkyl aluminum compound. Other cobalt salts may be used in which anions similar to chloride are present, and which may be removed by reaction with the Lewis or Bronsted acid. For instance cobalt halides, nitrates and carboxylates (such as acetates) may be used, particularly if they are slightly soluble in the process medium. It is preferred that these precursor cobalt salts be at least somewhat soluble in the process medium.

After the process has started, the complex may be in a form such as a compound of Formula IV

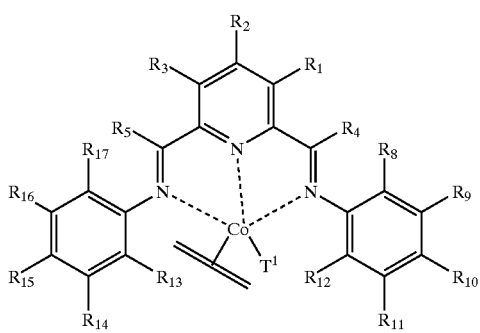

or a compound of Formula V

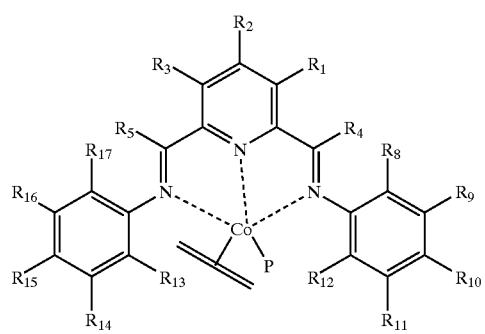

wherein, as before, the R groups are as defined above, and P is an alkyl group. It could at some time, especially at the beginning of the process, be $T^1$.

Compounds of formula I, III, IV and V may also be used, in the absence of any "co-catalysts" or "activators" to prepare alpha-olefins. Except for the ingredients in the process, the process conditions, such as temperature, medium, and the like, may be the same as for the other processes.

In all of the processes herein using olefins as a substrate, the temperature at which the processes are carried out is about 0° C. to about 100° C., and preferably about 10° C. to about 50° C.

The processes herein may be run in the presence of various liquids, particularly aprotic organic liquids. The catalyst system, olefin starting material, and alpha-olefin product may be soluble or insoluble in these liquids, but obviously these liquids should not prevent the processes from occurring. Suitable liquids include alkanes, alkenes, cycloalkanes, selected halogenated hydrocarbons, and aromatic hydrocarbons. Specific useful solvents include hexane, toluene, the alpha-olefins themselves, and benzene.

Suitable alpha-olefins to be employed in these processes include propylene, 1-butene, and the like.

The formation of the alpha-olefins as described herein is relatively rapid in many instances, and significant yields can be obtained in less than an hour. Under the correct conditions very high selectivity for an alpha-olefin is shown.

The alpha-olefins made herein may be further polymerized with other olefins to form polyolefins, especially linear low density polyethylenes. They may also be homopolymerized. These polymers may be made by a number of known methods, such as Ziegler-Natta-type polymerization, metallocene catalyzed polymerization, and other methods, see for instance World Patent Application 96/23010; see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, p. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylenes, and all of these references are herein incorporated by reference.

The alpha-olefins or internal olefins made herein may be converted to alcohols by known processes, these alcohols being useful for a variety of applications such as intermediates for detergents or plasticizers. The alpha-olefins may be converted to alcohols by a variety of processes, such as the oxo process followed by hydrogenation, or by a modified single step oxo process (the 'modified Shell process'), see for instance B. Elvers, et al., Ed., Ullmann's Encyclopedia of Chemical Technology, 5th Ed., Vol. A18, VCH Verlagsgesellschaft mbH, Weinheim, 1991, p. 321–327, the disclosure of which is herein incorporated by reference.

The products of the instant invention may also be employed as drilling fluid components.

The dimerizations and isomerizations herein may also initially be carried out in the solid state by, for instance, supporting an active catalyst or catalyst precursor on a substrate such as silica or alumina. Compounds of Formula IV and V have such a support indicated by the double line in the structure. If a catalyst precursor, such as a cobalt halide or nitrate, it may be activated with a Lewis (such as W, for instance an alkylaluminum compound) and exposing it to an alpha-olefin. Alternatively a solution of the catalyst precursor may be exposed to a support having an alkylaluminum compound on its surface. The support may also be able to take the place of the Lewis or Bronsted acid, for instance an acidic clay such as montmorillonite. Another method of making a supported catalyst is to start a polymerization or at least make a cobalt complex of another olefin or oligomer of an olefin such as cyclopentene on a support such as silica or alumina. All of these "heterogeneous" catalysts may be used to catalyze oligomerization in the liquid phase.

A dimerization process to form linear olefins comprises contacting an alpha-olefin with a cobalt complex of a tridentate bisimine pyridyl-type ligand having single alkyl-substituted or unsubstituted aryl groups that is activated with a bulky non-coordinating co-catalyst such as modified methylaluminoxane, MMAO. Concurrent isomerization of the alpha-olefins to internal olefins of the same carbon number gives a final product comprising linear dimers and internal olefins. Propylene dimerization provides an unexpected high yield of 1-hexene in addition to internal hexenes. The 1-hexene may be removed by distillation after the catalyst is deactivated. The remaining internal olefins are contacted with a catalyst under isomerization conditions to form additional 1-hexene that is removed continuously by distillation. Propylene is dimerized to a product containing 34% 1-hexene, 47% 2- and 3-hexenes, 15% nonenes and 5% heavies.

Another process may be employed to isomerize alpha-olefins selectively to internal olefins of the same carbon number without dimerization by contact with the cobalt complexes with a coordinating co-catalyst such as diethyl aluminum chloride, DEAC. Other suitable co-catalysts include modified methylalumoxane (MMAO), other aluminoxanes, and ethylaluminum dichloride (EADC). Preferred for the practice of the present invention is DEAC. A molar ratio of Al:Co is preferrably about 1:1 to about 200:1.

For 1-butene Dimerization:

After activation with a co-catalyst, the cobalt catalysts dimerize α-olefins with high productivity (TON 40,000). The cobalt-produced dimers are extremely linear (>97%) and contain only traces of trimeric species. The cobalt catalysts also have a tendency to isomerize α-olefins, as evidenced by the approximately equal levels of dimerization and isomerization achieved when 1-butene is dimerized. In fact, when the co-catalyst is changed to diethylaluminum chloride, isomerization occurs exclusively to give cis- and trans-2-olefins selectively.

For Propylene Dimerization:

To take advantage of the linear dimerization reaction and to mitigate the effects of feed isomerization, dimerizatiaon of propylene was also studied, with remarkable results. GC analysis of the products reveals a step-wise oligomerization process that makes linear hexenes, nonenes, and dodecenes. The hexenes are over 99% linear, and may contain over 50% of the valuable 1-hexene isomer, which can potentially be separated from the 2-hexene byproducts. Catalyst productivity is high (6500) lbs oligomer/lb Co compex; >2450 lbs oligomer/lb Al; 62,500 lbs oligomer/lb Co).

EXAMPLES

Abbreviations, Materials, and Sources of Materials:

| Abbreviations | |
|---|---|
| CPCHEM | Chevron-Phillips Chemical Company LP |

Materials

Cobalt (II) chloride hexahydrate, 2,6-diacetylpyridine, diethylaluminum chloride, and all aniline derivatives were purchased from Aldrich and used without further purification.

Polymer grade propylene in cylinders with dip tubes for transfer of liquefied gas was purchased from Matheson Gas Products, Inc.

Chevron-Phillips Chemical Company's commercial grade of 1-butene was used without purification.

Chevron-Phillips Chemical Company's 1-hexene was degassed and dried over 3A molecular sieves prior to use.

MMAO 3A was purchased from Akzo Nobel.

TABLE 1

Cobalt Complexes of Formula I

| Compound Number | R12 | R13 |
|---|---|---|
| Ia | Hydrogen | Hydrogen |
| Ib | Methyl | Methyl |
| Ic | Ethyl | Ethyl |
| Id | Isopropyl | Isopropyl |

Example 1

Preparation of Cobalt Complexes of Formula Ia–Id

Precatalyst complexes were synthesized, as were the ligands used to make the complexes.[5-7]

In general, the ligands were prepared by dissolving 2,6-diacetylpyridine and a slight excess (>2 eq.) of the appropriate aniline in methanol, heating the solution for one day under inert atmosphere with a catalytic amount of acetic acid, and recrystallizing the isolated solid from ethanol. The cobalt complexes were prepared by stirring a slight excess of the tridentate ligand with cobalt(II) chloride hexahydrate in THF for at least one day, then adding pentane to the solution and removing the precatalyst complexes by filtration. The complexes were all isolated in near-quantitative yield. Elemental analyses for complexes Ib–Id were carried out to determine the amount of THF in the isolated precatalysts. The solids were heated under vacuum at 40° C. prior to analysis. Complexes Ib and Ic tested positive for an equivalent of THF, but complex Id only contained trace amounts. Elemental analyses are reported as follows:

2,6-bis[1-(2-methylphenylimio)ethyl]pyridine cobalt(II) chloride.THF (Ib). Anal. Calcd. For $C_{27}H_{31}N_3Cl_2Oco$: C, 59.68; H, 5.75; O, 2.94. Found C, 59.00; H, 5.57; O, 2.33.

2,6-bis[1-(2-ethylphenylimino)ethyl]pyridine cobalt(II) chloride.THF (Ic). Anal. Calcd. For $C_{29}H_{35}N_3Cl_2OCo$: C, 60.95; H, 6.17; O, 2.80. Found C, 59.02; H, 5.80; O, 2.37.

2,6-bis[1-(2-isopropylphenylimio)ethyl]pyridine cobalt (II)chloride (Id). Anal. Calcd. For $C_{25}H_{27}N_3Cl_2Co$; C, 61.49; H, 5.92; O, 0.00. Found C, 60.91; H, 5.89; O, 0.16.

Example 2

Isomerization of 1-Hexene to 2-Hexene

Approximately 3.5 liters of 1-hexene was added to a 5L flask with stirring. The flask was fitted with a reflux condenser. The hexene was degassed overnight. 21 ml of modified methyl aluminum oxane (MMAO) (density 0.73) was added via syringe, then stirred for approximately 10 minutes. 110 mg of the cobalt complex was quickly added to the flask. The mixture then heated up from 22° C. to 39° C. within 2–3 minutes. A bucket of water was used to cool the reaction mixture. After 6 hours, 17% of 1-hexene remained. After 3 days, 70% of the mixture was converted to 2-hexene, 9% was converted to 3-hexene, and 20% was c-2-hexene.

Example 3

Procedure for Dimerization of Liquefied Gases

Under inert conditions, the appropriate cobalt complex was weighed out and added to an NMR tube. A small amount of methylene chloride was added to solublize the complex, and the tube was sealed. The sealed tube was then tied, using copper wire, to the internal cooling coils of a clean, dry Zipperclave™ reactor. The reactor was evacuated and then placed under static vacuum. A glass charger was then used to transfer the cocatalyst to the reactor, and the reactor was back-filled with Argon. The liquefied has cylinder was pressurized with a head pressure of Argon, and placed on a scale with ±5 g accuracy. Flexible hose was used to connect the gas cylinder to the reactor, and the desired amount of olefin was delivered to the reactor using the head pressure of the cylinder. The reactor was pressurized further with argon to ensure that the olefin remained in the liquid phase. Stirring was begun resulting in breakage of the NMR tube and activation of the catalyst. Reactor temperatures were easily maintained by internal or external cooling, depending on the desired reaction temperature.

ard 6890 Series GC System with an HP-5 50 m column with a 0.2 mm inner diameter was used for product characterization. Agilent ChemStation from Agilent Technologies was used to analyze the collected data. GC/MS data were obtained using an Agilent 5973 Benchtop Mass Spectrometer using electron impact ionization interfaced to an HP 6890 gas chromatograph. The GC column was a J&W Scientific DB-5MS, 60 m×0.25 mm i.d.

1-butene was dimerized in liquid phase to further assess the catalyst activity. The results of this reaction are reported below in Table 2. Unlike the analogous tridentate iron systems, these cobalt catalysts produce extremely low levels of methyl-branched heptenes in the octene products, resulting in 97%+ linearity in the dimers. Also, the cobalt systems make only traces of butene trimer, in comparison to the iron systems, which produce about 15% trimer. The systems may be activated with relatively low amounts of alumoxane cocatalysts (<100:1 Al:cat molar ratios).

TABLE 2

Dimerization of 1-Butene Using MMAO-Activated Cobalt Complexes Ic–Id

| Cat./ Mass (mg) | Al:Co Ratio | $C_4$ Mass (g) | T (° C.) | Rxn Length (h) | Prod. Mass (g) | % Conversion | Productivity (g dimer/g Co Complex) | % Linear Dimer | D/I Ratio[3] |
|---|---|---|---|---|---|---|---|---|---|
| 2/50 | 50 | 240 | 35 | 3 | 17 | 7 | 340 | 97 | 0.60 |
| 3/82 | 200 | 1080 | 20 | 5 | 340 | 31 | 4100 | 98 | 0.72 |
| 3/160 | 100 | 1500 | 20 | 18 | 157 | 17 | 1600 | 98 | 0.23 |
| 4/160 | 100 | 1500 | 20 | 18 | 124 | 8 | 780 | 98 | 0.14 | a) D/I ratio = mass ratio of (dimerized + trimerized butene)/isomerized butene

Example 4

Procedure for Dimerization/Isomerization of Liquid Olefins

Under inert conditions, the appropriate cobalt precatalyst was added to a dry flask with a stirbar. The alpha-olefin was then added, and rapid stirring was begun to slurry the complex. The flask was placed under a slight argon purge, and the cocatalyst was added via syringe. Temperatures were maintained by use of a water cooling bath.

After slowly adding water to deactivate the catalyst, an internal standard (if necessary) was added. A Hewlett Pack- As a further demonstration of the selectivity of the cobalt catalysts, the undimerized butene was examined. With the iron-based catalysts, the α-olefin feed was only lightly isomerized. With cobalt, however, complexes Ia–Id tended to isomerize the substrate heavily, resulting in the production of substantial quantities of 2-butene in the undimerized olefin. Isomerization occurs when an initial 2,1 (secondary) insertion of olefin is followed by β-elimination with opposite regiochemistry. For iron, initial 2,1 insertions tend to produce branched dimers, indicating that propagation is preferred; cobalt undergoes chain transfer following a 2,1 insertion, resulting in both highly linear dimers and high amounts of isomerization in the feed.

TABLE 3

Oligomerization of Propylene Using NMAO-Activated Cobalt Complexes of Formula Ia-Id change numbers

| Entry | Cat./ Mass (mg) | Al:Co Ratio | $C_3$ Mass (g) | T (° C.) | Rxn Length (h) | Prod. Mass (g) | % Conv. | Productivity (g olig./g Co complex) | Mass $C_6$ (g) | % Linear[a] | % 1-Hexene[b] | Mass $C_9$ (g)[c] |
|---|---|---|---|---|---|---|---|---|---|---|---|---|
| 1 | 2/30 | 100 | 250 | 0 | 5 | 13.7 | 5.5 | 460 | 10.4 | 97.4 | 17 | 1.9 |
| 2 | 2/30 | 100 | 250 | 30 | 5 | 171 | 68 | 5700 | 115 | 98.8 | 10 | 42.1 |
| 3 | 3/30 | 100 | 250 | 0 | 5 | 85.1 | 34 | 2840 | 63.5 | 99.5 | 59 | 17.7 |
| 4 | 3/30 | 100 | 250 | 20 | 5 | 97.5 | 39 | 3250 | 70.4 | 99.3 | 50 | 21.4 |
| 5 | 3/30 | 50 | 250 | 30 | 3 | 196 | 78 | 6540 | 105 | 99.3 | 37 | 62.1 |
| 6 | 4/30 | 100 | 250 | 20 | 21 | 92.1 | 37 | 3070 | 68.3 | 99.8 | 53 | 19.3 |
| 7 | 4/30 | 50 | 250 | 35 | 5 | 115 | 46 | 3830 | 81.6 | 99.6 | 54 | 23.9 |

TABLE 3-continued

Oligomerization of Propylene Using NMAO-Activated Cobalt
Complexes of Formula Ia-Id change numbers

| Entry | Cat./ Mass (mg) | Al:Co Ratio | C$_3$ Mass (g) | T (° C.) | Rxn Length (h) | Prod. Mass (g) | % Conv. | Productivity (g olig./g Co complex) | Mass C$_6$ (g) | % Linear[a] | % 1-Hexene[b] | Mass C$_9$ (g)[c] |
|---|---|---|---|---|---|---|---|---|---|---|---|---|
| 8 | 4/60 | 50 | 250 | 20 | 5 | 134 | 53 | 2230 | 88.4 | 99.8 | 51 | 33.2 |
| 9 | 4/60 | 50 | 250 | 35 | 5 | 117 | 47 | 1950 | 81.5 | 99.8 | 53 | 28.3 |

[a]% Linear = % linearity of the C$_6$ fraction
[b]% 1-Hexene = % 1-hexene in the C$_6$ fraction
[c]All of the nonene products contained significant quantities of 1-nonenes.
Entry 6, for example, contained 34% 1-nonene in the C$_9$ fraction.

To remove feed isomerization as a possibility, a study of propylene dimerization was undertaken, the results of which are summarized above in Table 3. The cobalt catalysts used in this study are less sterically bulky than those described previously[8]. The experiments in Table 3 employ cobalt catalysts bearing a single ortho substituent on each aryl ring, such as provided in Formula Ib, Ic, and Id and the results illustrate several unique trends. First, the catalysts are highly active, with catalyst productivities exceeding 6500 g product/g Co complex (~62,500 g product/g Co, entry 5). Second, the catalysts produce not only extremely linear dimers (FIG. 1), but the trimer products are also highly linear (FIG. 2). GC/MS analysis of the C$_9$ fraction made by catalyst of Formula Ic revealed over 95% linearity in the nonenes, a clear indicator that the C$_9$ and C$_{12}$ byproducts are formed by a step growth dimerization process (chain transfer following each insertion). As further evidence for a step growth process, analysis of the linear nonenes by GC/MS also did not reveal any 3-nonenes. Furthermore, the nonenes were even found to contain over 30% 1-nonenes in some instances, a result of codimerization of 1-hexene and propylene, with propylene involved in the second insertion step.

1-hexene was also made from propylene using these catalysts. Under the conditions employed, it was possible to isolate a propylene-based oligomer in which 70–75% of the products were n-hexenes with over 99.3% linearity. Of these hexenes, over 50% were the 1-hexene isomer, representing an overall product distribution that contained up to 45% 1-hexene for catalysts systems Ic and Id. With the major by-products in the hexene fraction being cis- and trans-2-hexene, and with only traces of other isomers present, separation of the high value and high purity 1-hexene is possible. In addition, the remaining olefins in the product stream (C$_6$ plus) are highly linear, and may be used in applications requiring sources of linear internal olefins.

The ratio of dimerization to isomerization varies dramatically depending on the activator used. For example, when complexes Ib-Id are activated with MMAO, dimerization and isomerization of the feed are competitive. When diethylaluminum chloride (DEAC) is used, isomerization occurs almost exclusively, resulting in the selective isomerization of 1-olefins to 2-olefins. These data are reported in Table 4. Rather than producing a thermodynamic distribution of internal olefin isomers from the α-olefin feed, the catalysts typically only move the double bond one position. After extended reaction times (up to and including days), the distribution is closer to thermodynamic, but the predominant olefin isomer remains the 2-olefin. When complex Ia, which bears no ortho alkyl groups on the aryl rings, is used as the catalyst, selective isomerization occurs regardless of whether MMAO or DEAC are employed as the activator. Table 4 below provides results on isomerization reactions using 1-hexene as the substrate. Other α-olefins may also be used.

TABLE 4

Isomerization of 1-Hexene Using
Cobalt Complexes of Formula Ia and Ib

| Cat./Mass (mg) | Cocat. | Al:Co ratio | Olefin/Amt (ml) | T (° C.) | Rxn length (h) | Product distribution (& each isomer) |
|---|---|---|---|---|---|---|
| 1/10 | MMAO | 115 | 1-hexene/50 | 35 | 2 | 1.9 1-hexene<br>62.4 t-2-hexene<br>34.2 c-2-hexene<br>1.0 other hexenes<br>0.6 dimer |
| 1/28 | MMAO | 60 | 1-hexene/50 | 5 | 1 | 1.1 1-hexene<br>77.5 t-2-hexene<br>19.9 c-2-hexene<br>0.9 other hexenes<br>0.5 dimer |
| 1/10 | DEAC | 40 | 1-hexene/50 | 25 | 18 | 1.0 1-hexene<br>62.9 t-2-hexene<br>15.4 c-2-hexene<br>20.5 3-hexenes |
| 2/27 | DEAC | 40 | 1-hexene/ | 25 | 72 | 1.0 1-hexene<br>61.2 t-2-hexene |

TABLE 4-continued

Isomerization of 1-Hexene Using
Cobalt Complexes of Formula Ia and Ib

| Cat./Mass (mg) | Cocat. | Al:Co ratio | Olefin/A mt (ml) | T (° C.) | Rxn length (h) | Product distribution (& each isomer) |
|---|---|---|---|---|---|---|
| | | | 100 | | | 15.5 c-2-hexene 22.0 3-hexenes 0.1 dimer |

All references are herein incorporated by reference.

REFERENCES (1) (a) Chauvin, Y.; Olivier, H. In applied *Homogeneous Catalysis with Organometallic Compounds*; Cornils, B.; Herrmann, W. Eds.; VCH: New York, 1996; Vol. 1, pp 258–268. (b) Skupinska, J. *Chem. Rev.* 1991, 91, 613. (c) Parshall, G. W.; Ittel, S. D. In *Homogeneous Catalysis, The Applications and Chemistry of Catalysis by Soluble Transition Metal Complexes*; John Wiley & Sons, Inc.: New York, 1992; $2^{nd}$ Ed., pp 72.85. (d) Bhaduri, S.; Mukesh, D. In *Homogeneous Catalysis, Mechanisms and Industrial Applications*; John Wiley & Sons, Inc.: New York, 2000; pp 142–147.

(2) Al-Jarallah, A. M.; Anabtawi, J. A.; Siddiqui, M. A. B.; Aitani, A. M.; Al-Sa'doun, A. W. *Catalysis Today,* 1992, 14(1).

(3) (a) Olivier-Bourbigou, H.; Chodorge, J. A.; Travers, P. *Petroleum Technology Quarterly,* 1999, Autumn, 141. (b) Chauvin, Y.; Gaillard, J. F.; Quang, D. V.; Andrews, J. W. *Chem. Ind.,* 1974, 375. (c) Commereuc, D.; Chauvin, Y.; Gaillard, J.; Léonard, J.; Andrews, J. W. *Hydrocarbon Process.* 1984, 118.

(4) (a) Small, B. L.; Marcucci, A. J. *Organometallics,* 2001, 20, 5738.

(5) For specific ligand syntheses, see the following references: (a) Small, B. L.; Brookhart, M. *J. Am. Chem. Soc.,* 1998, 120, 7143. (b) Alyea, E. C.; Merrill, P. H. *Syn. React. Inorg. Metal-Org. Chem.* 1974, 4(6), 535.

(6) For specific Co complex syntheses, see the following references: (a) Edwards, D. A.; Edwards, S. D.; Martin, W. R.; Pringle, T. J. *Polyhedron,* 1992, 11(13), 1569. (b) Britovsek, G. J. P.; Mastroianni, S.; Solan, G. A.; Baugh, S. P. D.; Redshaw, C.; Gibson, V. C.; White, A. J. P.; Williams, D. J.; Elsegood, M. R. J. *Chem. Euro. J.,* 2000, 6, No. 12, 2221.

(7) For general synthetic details for preparing pyridinebisimine cobalt complexes, see, for example, the following references: (a) Small, B. L.; Brookhart, M.; Bennett, A. M. A. *J. Am. Chem. Soc.,* 1998, 120, 4049. (b) Britovsek, G. J. P.; Gibson, V. C.; Kimberley, B. S.; Maddox, P. J.; McTavish, S. J.; Solan, G. A.; White, A. J. P.; Williams, D. J. *Chem. Commun.* 1998, 849. (c) Ittel, S. D.; Johnson, L. K.; Brookhart, M. *Chem. Rev.* 2000, 100, 1169. (d) Britovsek, G. J. P.; Gibson, V. C.; Wass, D. F. *Angew. Chem. Int. Ed.* 1999, 38, 428.

(8) Bennett, A. M. A. U.S. Pat. No. 6,063,881 (DuPont), 2000.

What is claimed is:

1. A process for the production of alpha-olefins comprising:

contacting a compound of Formula I:

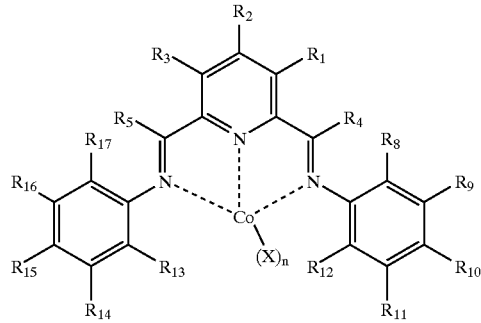

with an alpha-olefin and:
  (a) a first compound W, which is a neutral Lewis acid capable of abstracting $X^-$, an alkyl group, or a hydride group from Co to form $WX^-$, $(WR^{20})-$ or $WH^-$ and which is also capable of transferring an alkyl group or a hydride to Co, provided that $WX^-$ is a weakly coordinating anion; or
  (b) a combination of second compound which is capable of transferring an alkyl or hydride group to Co and a third compound which is a neutral Lewis acid which is capable of abstracting $X^-$, a hydride or an alkyl group from Co to form a weakly coordinating anion;

wherein:
  each X is an anion;
  n is 1, 2 or 3 so that the total number of negative charges on said anion or anions is equal to the oxidation state of a Co atom present in Formula I;
  $R_1$, $R_2$ and $R_3$ are each independently hydrogen, hydrocarbyl, substituted hydrocarbyl, or an inert functional group;
  $R_4$ and $R_5$ are each independently hydrogen, hydrocarbyl, an inert functional group or substituted hydrocarbyl;
  $R_9$, $R_{10}$, $R_{11}$, $R_{14}$, $R_{15}$ and $R_{16}$ are each independently hydrogen, hydrocarbyl, an inert functional group or substituted hydrocarbyl;
  $R_8$ and $R_{17}$ are each hydrogen, fluorine, an inert functional group, a primary carbon group, a secondary carbon group or a tertiary carbon group; and
  $R_{20}$ is alkyl;

and provided that:
  when $R_8$ is a primary carbon group none, one or two of $R_{12}$, $R_{13}$ and $R_{17}$ are primary carbon groups, secondary carbon groups, or inert functional groups, and the remainder of $R_{12}$, $R_{13}$, and $R_{17}$ are hydrogen or fluorine;
  when $R_8$ is a secondary carbon group, none or one or two of $R_{12}$, $R_{13}$ and $R_{17}$ is a primary carbon group or a secondary carbon group or an inert functional group and the remainder of $R_{12}$, $R_{13}$ and $R_{17}$ are hydrogen or fluorine;

when $R_8$ is a tertiary carbon group all of $R_{12}$, $R_{13}$, and $R_{17}$ are hydrogen or fluorine; and any two of $R_8$, $R_9$, $R_{10}$, $R_{11}$, $R_{12}$, $R_{13}$, $R_{14}$, $R_{15}$, $R_{16}$ and $R_{17}$ vicinal to one another, taken together may form a ring.

2. The process of claim 1 wherein:

$R_4$ and $R_5$ are methyl or hydrogen;

$R_1$, $R_2$, and $R_3$ are all hydrogen;

$R_9$, $R_{10}$, $R_{11}$, $R_{12}$, $R_{13}$, $R_{14}$, $R_{15}$ and $R_{16}$ are all hydrogen; and $R_8$ and $R_{17}$ are each independently methyl, ethyl, propyl, or isopropyl.

3. The process of claim 1 wherein:

$R_4$ and $R_5$ are methyl or hydrogen;

$R_{12}$ and $R_{13}$ are hydrogen; and $R_8$ and $R_{17}$ are each independently methyl, ethyl, propyl or isopropyl.

4. The process of claim 1 wherein:

$R_4$ and $R_5$ are methyl or hydrogen;

$R_{12}$ and $R_{13}$ are hydrogen; and $R_8$ and $R_{17}$ are both methyl.

5. The process of claim 2 wherein $R_8$ and $R_{17}$ are both methyl or ethyl.

6. The process of claim 2 wherein:

$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both methyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

7. The process of claim 1 wherein the temperature is about 0° C. to about 100° C.

8. The process of claim 1 wherein the temperature is about 10° C. to about 50° C.

9. The process of claim 1 wherein W is an alkyl aluminum compound.

10. The process of claim 9 wherein said alkyl aluminum compound is an alkyl aluminoxane.

11. The process of claim 1 wherein:

if $R_8$ is a primary carbon group, $R_{13}$ is a primary carbon group and $R_{12}$ and $R_{17}$ are hydrogen; or if $R_8$ is a secondary carbon group, $R_{13}$ is a primary or secondary carbon group, and $R_{12}$ and $R_{17}$ are hydrogen.

12. A process for the production of alpha-olefins, comprising:

contacting a Co[I] or Co[II] or Co[III] complex of a tridentate ligand of Formula II with an alpha-olefin,

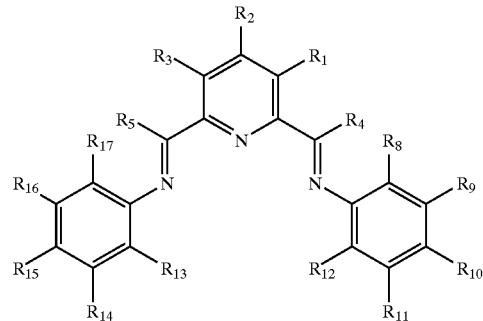

wherein $R_1$, $R_2$ and $R_3$ are each independently hydrogen, fluorine, hydrocarbyl, substituted hydrocarbyl, or an inert functional group;

$R_4$ and $R_5$ are each independently hydrogen, hydrocarbyl, an inert functional group or substituted hydrocarbyl;

$R_9$, $R_{10}$, $R_{11}$, $R_{14}$, $R_{15}$ and $R_{16}$ are each independently hydrogen, hydrocarbyl, an inert functional group or substituted hydrocarbyl;

$R_8$ and $R_{17}$ are each hydrogen, fluorine, an inert functional group, a primary carbon group, a secondary carbon group or a tertiary carbon group;

and provided that:

when $R_8$ is a primary carbon group none, one or two of $R_{12}$, $R_{13}$ and $R_{17}$ are primary carbon groups, and the remainder of $R_{12}$, $R_{13}$ and $R_{17}$ are hydrogen or fluorine;

when $R_8$ is a secondary carbon group, none or one or two of $R_{12}$, $R_{13}$ and $R_{17}$ is a primary carbon group or a secondary carbon group or an inert functional group and the remainder of $R_{12}$, $R_{13}$, and $R_{17}$ are hydrogen or fluorine;

when $R_8$ is a tertiary carbon group all of $R_{12}$, $R_{13}$ and $R_{17}$ are hydrogen or fluorine;

any two of $R_8$, $R_9$, $R_{10}$, $R_{11}$, $R_{12}$, $R_{13}$, $R_{14}$, $R_{15}$, $R_{16}$ and $R_{17}$ vicinal to one another, taken together may form a ring;

a Co[I] or Co[II] or Co[III] atom also has bonded to it an empty coordination site or a ligand that may be displaced by said alpha-olefin, and a ligand that may add to said alpha-olefin.

13. The process of claim 12 wherein:

$R_4$ and $R_5$ are methyl or hydrogen;

$R_1$, $R_2$, and $R_3$ are all hydrogen;

$R_9$, $R_{10}$, $R_{11}$, $R_{12}$, $R_{13}$, $R_{14}$, $R_{15}$ and $R_{16}$ are all hydrogen; and $R_8$ and $R_{17}$ are each independently methyl, ethyl, propyl or isopropyl.

14. The process of claim 12 wherein:

$R_4$ and $R_5$ are methyl or hydrogen; and $R_8$ and $R_{17}$ are each independently methyl, ethyl, propyl or isopropyl.

15. The process of claim 12 wherein:

$R_4$ and $R_5$ are methyl or hydrogen; and $R_8$ and $R_{17}$ are both methyl or ethyl.

16. The process of claim 13 wherein $R_8$ and $R_{17}$ are both methyl or ethyl.

17. The process of claim 12 wherein:

$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$, and $R_{17}$ are both methyl; or

19

$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

18. The process of claim 12 wherein said temperature is about 0° C. to about 100° C.

19. The process of claim 12 wherein:

if $R_8$ is a primary carbon group, $R_{13}$ is a primary carbon group and $R_{12}$ and $R_{17}$ are hydrogen; or if $R_8$ is a secondary carbon group, $R_{13}$ is a primary or secondary carbon group, and $R_{12}$ and $R_{13}$ are hydrogen.

20. A process for the production of alpha-olefins, comprising:

contacting an alpha-olefin and a compound of Formula III, Formula IV, or Formula V:

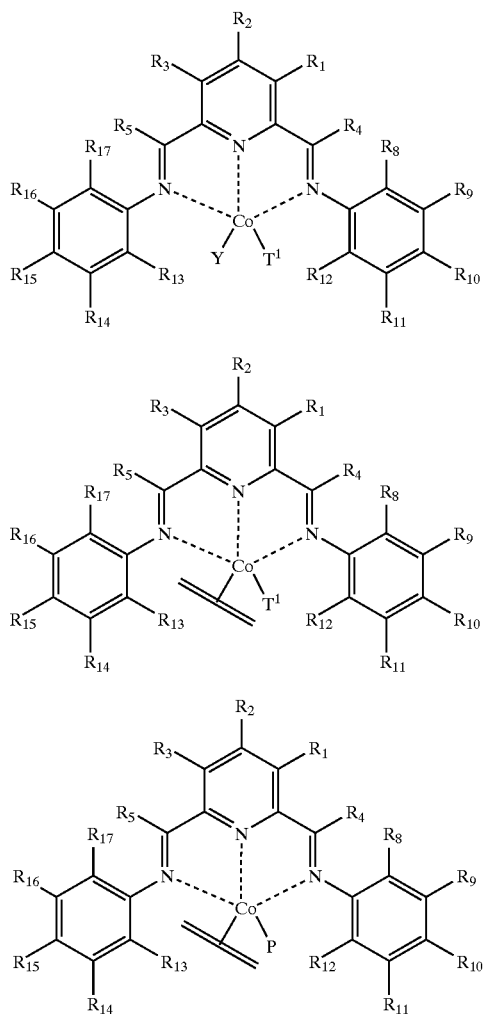

wherein:

$R_1$, $R_2$ and $R_3$ are each independently hydrogen, hydrocarbyl, substituted hydrocarbyl, or an inert functional group;

20

$R_4$ and $R_5$ are each independently hydrogen, hydrocarbyl, an inert functional group, or substituted hydrocarbyl, $R_9$, $R_{10}$, $R_{11}$, $R_{14}$, $R_{15}$ and $R_{16}$ are each independently hydrogen, hydrocarbyl, an inert functional group, or substituted hydrocarbyl;

$R_8$ and $R_{17}$ are each hydrogen, fluorine, an inert functional group, a primary carbon group, a secondary carbon group or a tertiary carbon group;

$T^1$ is hydride or alkyl or any other anionic ligand into which an alpha-olefin can insert;

Y is a vacant coordination site, or a neutral ligand capable of being displaced by an alpha-olefin; and P is an alkyl group;

and provided that:

when $R_8$ is a primary carbon group none, one or two of $R_{12}$, $R_{13}$ and $R_{17}$ are primary carbon groups, and the remainder of $R_{12}$, $R_{13}$ and $R_{17}$ are hydrogen or fluorine; when $R_8$ is a secondary carbon group, none or one of $R_{12}$, $R_{13}$ and $R_{17}$ is a primary carbon group or a secondary carbon group and the remainder of $R_{12}$, $R_{13}$, and $R_{17}$ are hydrogen or fluorine;

when $R_8$ is a tertiary carbon group all of $R_{12}$, $R_{13}$ and $R_{17}$ are hydrogen or fluorine; and any two of $R_8$, $R_9$, $R_{10}$, $R_{11}$, $R_{12}$, $R_{13}$, $R_{14}$, $R_{15}$, $R_{16}$ and $R_{17}$ vicinal to one another, taken together may form a ring.

21. The process of claim 20 wherein:

$R_4$ and $R_5$ are methyl or hydrogen;

$R_1$, $R_2$, and $R_3$ are all hydrogen;

$R_9$, $R_{10}$, $R_{11}$, $R_{12}$, $R_{13}$, $R_{14}$, $R_{15}$ and $R_{16}$ are all hydrogen; and $R_8$ and $R_{17}$ are each independently methyl, ethyl, propyl or isopropyl.

22. The process of claim 20 wherein:

$R_4$ and $R_5$ are methyl or hydrogen; and $R_8$ and $R_{17}$ are each independently methyl, ethyl, propyl or isopropyl.

23. The process of claim 20 wherein:

$R_4$ and $R_5$ are methyl or hydrogen; and $R_8$ and $R_{17}$ are both methyl or ethyl.

24. The process of claim 20 wherein $R_8$ and $R_{17}$ are both methyl or ethyl.

25. The process of claim 20 wherein:

$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both methyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

26. The process of claim 20 wherein said temperature is about 0° C. to about 100° C.

27. The process of claim 20 wherein said compound is a compound of Formula III.

28. The process of claim 20 wherein said compound is a compound of Formula IV.

29. The process of claim 20 wherein said compound is a compound of Formula V.

30. The process of claim 20 wherein:
if $R_8$ is a primary carbon group, $R_{13}$ is a primary carbon group and $R_{12}$ and $R_{17}$ are hydrogen; or
if $R_8$ is a secondary carbon group, $R_{13}$ is a primary or secondary carbon group, and $R_{12}$ and $R_{17}$ are hydrogen.

31. The process of claim 1 wherein said compound is or becomes part of a heterogeneous catalyst on a solid support.

32. The process of claim 12 wherein said complex is or becomes part of a heterogeneous catalyst on a solid support.

33. The process of claim 20 wherein said complex is or becomes part of a heterogeneous catalyst on a solid support.

34. A process for the dimerization of alpha-olefins comprising:
contacting a compound of Formula I:

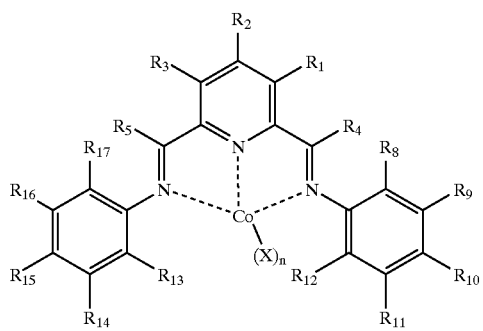

with an alpha-olefin and:
(a) a first compound W, which is a neutral Lewis acid capable of abstracting X−, an alkyl group, or a hydride group from Co to form WX−, (WR20)− or WH− and which is also capable of transferring an alkyl group or a hydride to Co, provided that WX− is a weakly coordinating anion; or
(b) a combination of second compound which is capable of transferring an alkyl or hydride group to Co and a third compound which is a neutral Lewis acid which is capable of abstracting X−, a hydride or an alkyl group from Co to form a weakly coordinating anion;
wherein:
each X is an anion;
n is 1, 2 or 3 so that the total number of negative charges on said anion or anions is equal to the oxidation state of a Co atom present in Formula I;
$R_1$, $R_2$ and $R_3$ are each independently hydrogen, hydrocarbyl, substituted hydrocarbyl, or an inert functional group;
$R_4$ and $R_5$ are each independently hydrogen, hydrocarbyl, an inert functional group or substituted hydrocarbyl;
$R_9$, $R_{10}$, $R_{11}$, $R_{14}$, $R_{15}$ and $R_{16}$ are each independently hydrogen, hydrocarbyl, an inert functional group or substituted hydrocarbyl;
$R_8$ and $R_{17}$ are each hydrogen, fluorine, an inert functional group, a primary carbon group, a secondary carbon group or a tertiary carbon group; and
$R_{20}$ is alkyl;
and provided that:
when $R_8$ is a primary carbon group none, one or two of $R_{12}$, $R_{13}$ and $R_{17}$ are primary carbon groups, secondary carbon groups, or inert functional groups, and the remainder of $R_{12}$, $R_{13}$, and $R_{17}$ are hydrogen or fluorine;

when $R_8$ is a secondary carbon group, none or one or two of $R_{12}$, $R_{13}$ and $R_{17}$ is a primary carbon group or a secondary carbon group or an inert functional group and the remainder of $R_{12}$, $R_{13}$, and $R_{17}$ are hydrogen or fluorine;

when $R_8$ is a tertiary carbon group all of $R_{12}$, $R_{13}$, and $R_{17}$ are hydrogen or fluorine; and any two of $R_8$, $R_9$, $R_{10}$, $R_{11}$, $R_{12}$, $R_{13}$, $R_{14}$, $R_{15}$, $R_{16}$ and $R_{17}$ vicinal to one another, taken together may form a ring.

35. The process of claim 34 wherein:
$R_4$ and $R_5$ are methyl or hydrogen;
$R_1$, $R_2$, and $R_3$ are all hydrogen;
$R_9$, $R_{10}$, $R_{11}$, $R_{12}$, $R_{13}$, $R_{14}$, $R_{15}$ and $R_{16}$ are all hydrogen; and
$R_8$ and $R_{17}$ are each independently methyl, ethyl, propyl, or isopropyl.

36. The process of claim 34 wherein:
$R_4$ and $R_5$ are methyl or hydrogen;
$R_{12}$ and $R_{13}$ are hydrogen; and
$R_8$ and $R_{17}$ are each independently methyl, ethyl, propyl or isopropyl.

37. The process of claim 34 wherein:
$R_4$ and $R_5$ are methyl or hydrogen;
$R_{12}$ and $R_{13}$ are hydrogen; and
$R_8$ and $R_{17}$ are both methyl.

38. The process of claim 35 wherein $R_8$ and $R_{17}$ are both methyl or ethyl.

39. The process of claim 35 wherein:
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both methyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

40. The process of claim 34 wherein the temperature is about 0° C. to about 100° C.

41. The process of claim 34 wherein the temperature is about 10° C. to about 50° C.

42. The process of claim 34 wherein W is an alkyl aluminum compound.

43. The process of claim 42 wherein said alkyl aluminum compound is an alkyl aluminoxane.

44. The process of claim 34 wherein:
if $R_8$ is a primary carbon group, $R_{13}$ is a primary carbon group and $R_{12}$ and $R_{17}$ are hydrogen; or
if $R_8$ is a secondary carbon group, $R_{13}$ is a primary or secondary carbon group, and $R_{12}$ and $R_{17}$ are hydrogen.

45. A process for the isomerization of alpha-olefins to internal olefins comprising:

contacting a compound of Formula I:

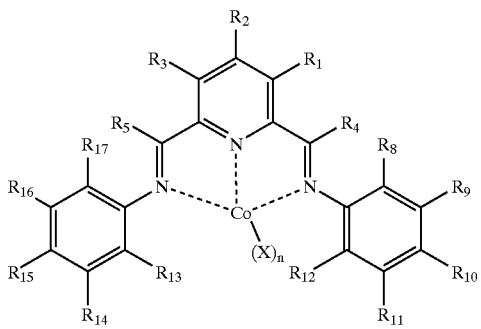

with an alpha-olefin and:
(a) a first compound W, which is a neutral Lewis acid capable of abstracting X−, an alkyl group, or a hydride group from Co to form WX−, (WR20)− or WH− and which is also capable of transferring an alkyl group or a hydride to Co, provided that WX− is a weakly coordinating anion; or
(b) a combination of second compound which is capable of transferring an alkyl or hydride group to Co and a third compound which is a neutral Lewis acid which is capable of abstracting X−, a hydride or an alkyl group from Co to form a weakly coordinating anion;

wherein:
each X is an anion;
n is 1, 2 or 3 so that the total number of negative charges on said anion or anions is equal to the oxidation state of a Co atom present in Formula I;
$R_1$, $R_2$ and $R_3$ are each independently hydrogen, hydrocarbyl, substituted hydrocarbyl, or an inert functional group;
$R_4$ and $R_5$ are each independently hydrogen, hydrocarbyl, an inert functional group or substituted hydrocarbyl;
$R_9$, $R_{10}$, $R_{11}$, $R_{14}$, $R_{15}$ and $R_{16}$ are each independently hydrogen, hydrocacbyl, an inert functional group or substituted hydrocarbyl;
$R_8$ and $R_{17}$ are each hydrogen, fluorine, an inert functional group, a primary carbon group, a secondary carbon group or a tertiary carbon group; and
$R_{20}$ is alkyl;
and provided that:
when $R_8$ is a primary carbon group none, one or two of $R_{12}$, $R_{13}$ and $R_{17}$ are primary carbon groups, secondary carbon groups, or inert functional groups, and the remainder of $R_{12}$, $R_{13}$, and $R_{17}$ are hydrogen or fluorine;
when $R_8$ is a secondary carbon group, none or one or two of $R_{12}$, $R_{13}$ and $R_{17}$ is a primary carbon group or a secondary carbon group or an inert functional group and the remainder of $R_{12}$, $R_{13}$, and $R_{17}$ are hydrogen or fluorine;
when $R_8$ is a tertiary carbon group all of $R_{12}$, $R_{13}$, and $R_{17}$ are hydrogen or fluorine; and
any two of $R_8$, $R_9$, $R_{10}$, $R_{11}$, $R_{12}$, $R_{13}$, $R_{14}$, $R_{15}$, $R_{16}$ and $R_{17}$ vicinal to one another, taken together may form a ring.

46. The process of claim 45 wherein:
$R_4$ and $R_5$ are methyl or hydrogen;
$R_1$, $R_2$, and $R_3$ are all hydrogen;
$R_9$, $R_{10}$, $R_{11}$, $R_{12}$, $R_{13}$, $R_{14}$, $R_{15}$ and $R_{16}$ are all hydrogen; and $R_8$ and $R_{17}$ are each independently methyl, ethyl, propyl, or isopropyl.

47. The process of claim 45 wherein:
$R_4$ and $R_5$ are methyl or hydrogen;
$R_{12}$ and $R_{13}$ are hydrogen; and
$R_8$ and $R_{17}$ are each independently methyl, ethyl, propyl or isopropyl.

48. The process of claim 45 wherein:
$R_4$ and $R_5$ are methyl or hydrogen;
$R_{12}$ and $R_{13}$ are hydrogen; and
$R_8$ and $R_{17}$ are both methyl.

49. The process of claim 46 wherein $R_8$ and $R_{17}$ are both methyl or ethyl.

50. The process of claim 46 wherein:
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both methyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or
$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

51. The process of claim 46 wherein the temperature is about 0° C. to about 100° C.

52. The process of claim 46 wherein the temperature is about 10° C. to about 50° C.

53. The process of claim 45 wherein W is an alkyl aluminum compound.

54. The process of claim 53 wherein said alkyl aluminum compound is an alkyl aluminoxane.

55. The process of claim 45 wherein:
if $R_8$ is a primary carbon group, $R_{13}$ is a primary carbon group and $R_{12}$ and $R_{17}$ are hydrogen; or
if $R_8$ is a secondary carbon group, $R_{13}$ is a primary or secondary carbon group, and $R_{12}$ and $R_{17}$ are hydrogen.

56. A process for oligomerizing alpha-olefins comprising:
contacting a compound of Formula I:

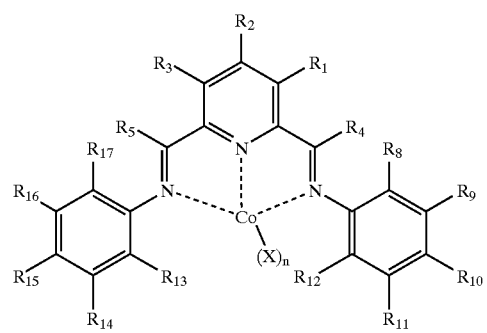

with an alpha-olefin wherein if said olefin is propylene, then the oligomerization process proceeds by a step growth mechanism, and:
(a) a first compound W, which is a neutral Lewis acid capable of abstracting X−, an alkyl group, or a hydride group from Co to form WX−, (WR20)− and which is also capable of transferring an alkyl group or a hydride to Co, provided that WX− is a weakly coordinating anion; or (b) a combination of second compound which is capable of transferring an alkyl or hydride group to Co and a third compound which is neutral Lewis acid which is capable of abstracting X−, a hydride or an alkyl group from Co to form a weakly coordinating anion;

wherein each X is an anion;

n is 1, 2 or 3 so that the total number of negative charges on said anion or anions is equal to the oxidation state of a Co atom present in Formula I;

$R_1$, $R_2$ and $R_3$ are each independently hydrogen, hydrocarbyl, substituted hydrocarbyl, or an inert functional group;

$R_4$ and $R_5$ are each independently hydrogen, hydrocarbyl, and inert functional group or substituted hydrocarbyl;

$R_9$, $R_{10}$, $R_{11}$, $R_{14}$, $R_{15}$ and $R_{16}$ are each independently hhydrogen, hydrocarbyl, an inert functional group or substituted hydrocarbyl;

$R_8$ and $R_{17}$ are each hydrogen, fluorine, an inert functional group, a primary carbon group, a secondary carbon group or a tertiary carbon group; and $R_{20}$ is alkyl;

and provided that:

when $R_8$ is a primary carbon group none, one or two of $R_{12}$, $R_{13}$, and $R_{17}$ are primary carbon groups, secondary carbon groups, or inert functional groups, and the remainder of $R_{12}$, $R_{13}$, and $R_{17}$ are hydrogen or fluorine;

when $R_8$ is a secondary carbon group, none or one or two of $R_{12}$, $R_{13}$ and $R_{17}$ is a primary carbon group or a secondary carbon group or an inert functional group and the remainder of $R_{12}$, $R_{13}$, and $R_{17}$ are hydrogen or fluorine;

when $R_8$ is a tertiary carbon group all of $R_{12}$, $R_{13}$, and $R_{17}$ are hydrogen or fluorine; and any two of $R_8$, $R_9$, $R_{10}$, $R_{11}$, $R_{12}$, $R_{13}$, $R_{14}$, $R_{15}$ and $R_{16}$ vicinal to one another, taken together may form a ring.

57. The process of claim 56 wherein:

$R_4$ and $R_5$ are methyl or hydrogen;

$R_1$, $R_2$, and $R_3$ are all hydrogen;

$R_9$, $R_{10}$, $R_{11}$, $R_{12}$, $R_{13}$, $R_{14}$, $R_{15}$ and $R_{16}$ are all hydrogen; and $R_8$ and $R_{17}$ are each independently methyl, ethyl, propyl, or isopropyl.

58. The process of claim 56 wherein:

$R_4$ and $R_5$ are methyl or hydrogen;

$R_{12}$ and $R_{13}$ are hydrogen; and $R_8$ and $R_{17}$ are each independently methyl, ethyl, propyl or isopropyl.

59. The process of claim 56 wherein:

$R_4$ and $R_5$ are methyl or hydrogen;

$R_{12}$ and $R_{13}$ are hydrogen; and $R_8$ and $R_{17}$ are both methyl.

60. The process of claim 57 wherein $R_8$ and $R_{17}$ are both methyl or ethyl.

61. The process of claim 57 wherein:

$R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both methyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both ethyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both isopropyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both n-propyl; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both chloro; or $R_4$ and $R_5$ are methyl, $R_9$, $R_{10}$, $R_{11}$, $R_{12}$, $R_{13}$, $R_{14}$, $R_{15}$ and $R_{16}$ are all hydrogen, $R_8$ and $R_{17}$ are both trifluoromethyl.

62. The process of claim 56 wherein the temperature is about 0° C. to about 100° C.

63. The process of claim 56 wherein the temperature is about 10° C. to about 50° C.

64. The process of claim 56 wherein W is an alkyl aluminum compound.

65. The process of claim 64 wherein said alkyl aluminum compound is an alkyl aluminoxane.

66. The process of claim 56 wherein:

if $R_8$ is a primary carbon group, $R_{13}$ is a primary carbon group and $R_{12}$ and $R_{17}$ are hydrogen; or if $R_8$ is a secondary carbon group, $R_{13}$ is a primary or secondary carbon group, and $R_{12}$ and $R_{17}$ are hydrogen.

67. The process of claims 1, 34, 45, or 56 wherein a pressurized inert gas is used to liquify the olefin.

68. The process of claim 34 which produces alpha-olefin dimers possessing >90% linearity.

69. The process of claim 45 which isomerizes alpha-olefins selectively to make 2-olefins.

70. The process of claim 45 wherein 80% of the isomerized olefin is 2-olefin.

71. The process of claim 56 wherein a propylene trimer is produced with >70% linearity.

72. The process of claim 56 wherein a propylene tetramer is produced with >70% linearity.

73. The process of claim 56 wherein a propylene trimer is produced with >90% linearity.

74. The process of claim 34 wherein a propylene dimer is produced with >90% linearity.

75. The process of claim 56 wherein propylene oligomers with a total branch index of >0.1 are produced.

76. The process of claim 56 wherein propylene oligomers with a total branch index of >0.1 (>0.1 branch per oligomer product molecule) are produced.

77. The process of claim 45 wherein an isomerized alpha-olefin is produced.

78. The process of claim 34 wherein an olefin dimer is produced.

79. The process of claim 56 wherein an olefin oligomer is produced.

80. The process of claim 34 wherein an olefin dimer possessing at least 90% linearity is produced.

81. The process of claim 56 wherein the oligomerization propylene occurs via a step-growth mechanism.

82. The process of claim 1 wherein 1-hexene is produced from propylene.

83. The process of claim 1 wherein a linear propylene dimer consisting of essentially 99% 1-hexene or 2-hexene is prepared.

84. The process of claim 1 wherein a linear propylene trimer containing at least 10% 1-nonene is prepared.

85. The process of claim 56, in which a second step is used to convert the linear product into alcohols.

86. The process of claim 56 wherein a second step is used to convert the linear product into a PAO or PIO (poly alpha-olefin or poly internal olefin).

87. The process of claim 56 wherein a second step is used to convert the linear product into a carboxylic acid.

88. The process of claim 56 wherein a second step is used to convert the linear product into an LAB (linear alkyl benzene).

89. The process of claim 56 wherein a second step is used to employ the products as comonomer for the production of polyethylene.

90. The process of claim 56 wherein a second step is used to convert the linear product into an FDF (functional drilling fluid).

91. The process of claim 56 wherein a second step is used to convert the linear product into an ASA (alkyl succinic anhydride).

92. The process of claim 56 wherein a second step is used to convert the linear product into an olefin sulfonate.

93. The process of claim 1 wherein a propylene dimer possessing greater than 98% linearity is prepared.

* * * * *